United States Patent [19]

Shah et al.

[11] Patent Number: 4,758,630
[45] Date of Patent: Jul. 19, 1988

[54] DENTURE STABILIZING ZINC AND STRONTIUM SALTS OF AVE/MA COPOLYMER

[75] Inventors: Nutan B. Shah; Michael C. Gounaris, both of Huntington; Kenneth T. Holeva, Waterbury, all of Conn.

[73] Assignee: Richardson-Vicks Inc., Wilton, Conn.

[21] Appl. No.: 923,619

[22] Filed: Oct. 27, 1986

[51] Int. Cl.$^4$ ................................................ C08F 8/44
[52] U.S. Cl. ...................................... 525/207; 523/120; 525/327.9; 525/328.9; 525/366; 525/370
[58] Field of Search .................. 525/207, 327.8, 328.9

[56] References Cited

U.S. PATENT DOCUMENTS

| | | | |
|---|---|---|---|
| 3,003,988 | 10/1961 | Germann et al. | 525/327.8 |
| 3,436,378 | 4/1969 | Azorlosa et al. | 525/327.8 |
| 3,451,890 | 6/1969 | Stump, Jr. | 525/327.8 |
| 3,499,876 | 3/1970 | Field et al. | 525/327.8 |
| 3,786,012 | 1/1974 | Marion et al. | 525/327.8 |
| 4,071,669 | 1/1978 | Tazuma et al. | 525/327.8 |
| 4,359,047 | 11/1982 | Potaczek | 525/328.9 |
| 4,387,186 | 6/1983 | Williams et al. | 525/327.8 |
| 4,396,471 | 8/1983 | Fletcher et al. | 525/327.8 |
| 4,506,041 | 3/1985 | Tanigawa et al. | 525/327.8 |

FOREIGN PATENT DOCUMENTS

| | | |
|---|---|---|
| 0068847 | 1/1983 | European Pat. Off. . |
| 1245011 | 9/1971 | United Kingdom . |

*Primary Examiner*—Joseph L. Schoffer
*Assistant Examiner*—Bernard Lipman
*Attorney, Agent, or Firm*—Salvatore R. Conte; David K. Dabbiere; Douglas C. Mohl

[57] ABSTRACT

Zinc and strontium unmixed partial salts of lower alkyl vinyl ether-maleic acid copolymers useful as denture adhesives.

19 Claims, No Drawings

DENTURE STABILIZING ZINC AND STRONTIUM SALTS OF AVE/MA COPOLYMER

SUMMARY OF THE INVENTION

In U.S. Pat. No. 3,003,988, issued to D. P. Germann et al and entitled "Stabilizer for Dentures", there are described certain water-sensitized, but water-insoluble, materials for stabilizing dentures which are synthetic, hydrophilic, colloidal materials comprising mixed partial salts and esters of lower alkyl (1 to 4 carbons) vinyl ether-maleic anhydride-type copolymers, said mixed partial salts and esters containing both divalent calcium and monovalent alkali (i.e., sodium, potassium and ammonium) cations.

The instant invention, which also provides highly effective denture stabilizing materials, relates to zinc and strontium partial salts of lower alkyl ($C_{1-4}$) vinyl ether-maleic acid copolymers, wherein said zinc and strontium cations are "unmixed" with any other cations or ester functions in the copolymeric salt, the remaining initial carboxyl groups being unreacted. Said lower alkyl vinyl ether-maleic acid copolymer may be referred to hereinafter by the abbreviated term "AVE/MA copolymer" and the preferred methyl vinyl ether-maleic acid copolymer as "MVE/MA copolymer".

DETAILED DESCRIPTION OF THE INVENTION

The novel synthetic materials of the instant invention are partial zinc and strontium metal salts of lower alkyl vinyl ether-maleic acid (AVE/MA) copolymers, said copolymers consisting essentially of the repeated structural unit:

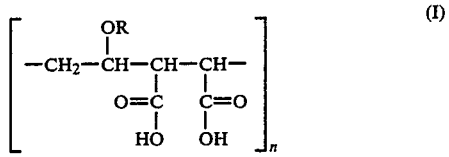

(I)

wherein R represents an alkyl radical of 1 to 4 carbon atoms (methyl preferred), n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing a member selected from the group consisting of zinc (preferred) or strontium cations as the sole cationic salt function, with from about 10 to about 60 percent and, preferably, from about 40 to about 50 percent, of the total initial carboxyl groups reacted with said cations.

The subject polymeric salts are advantageously prepared by the interaction of the AVE/MA copolymer (I) with a cationic zinc or strontium compound having a functional group typical of reactants of carboxylic acid, such as, for example, the hydroxide, acetate, halide, lactate, etc., in an aqueous medium. In a preferred embodiment, the or oxide of zinc is utilized. Since zinc hydroxide is not commercially available, its use as a reactant is readily and more economically accomplished by employing an aqueous slurry of particulate zinc oxide which, although practically insoluble in water, provides hydration to zinc hydroxide on the particulate surface. Strontium hydroxide, on the other hand, is available in either crystalline or powder form and is soluble in about 50 parts water. Aqueous solutions of strontium oxide, however, which forms the hydroxide when treated with water (caution: heat evolution), may also be used.

Anions that form toxic, irritating or contaminating by-products should be avoided, or special precautions and treatment provided to assure the removal and absence of such by-products from the polymeric salt end-product. The particular compound used should be substantially pure to assure obtaining a substantially pure, substantially off-white polymeric salt end-product.

The lower alkyl vinyl ether-maleic acid (AVE/MA) copolymers (I) are readily obtained by copolymerizing a lower alkyl vinyl ether monomer, such as methyl vinyl ether, ethyl vinyl ether, divinyl ether, propyl vinyl ether and isobutyl vinyl ether, with maleic anhydride to yield the corresponding lower alkyl vinyl ether-maleic anhydride copolymer which is readily hydrolyzable to the acid copolymer (I). Both anhydride and acid forms are also available from commercial suppliers. For example, the GAF Corporation, Wayne, N.J., provides both the polymeric free acid form (I) and the corresponding anhydride form under its "GANTREZ" trademark as the "GANTREZ S Series" and "GANTREZ AN Series", respectively. In the former acid series, the GANTREZ S-97 (M.W.=50,000) is particularly suitable, and, in the latter anhydride series, the GANTREZ AN-149 (M.W.=50,000), the GANTREZ AN-169 (M.W.=67,000) and the GANTREZ AN-179 (M.W.=80,000) copolymers are particularly suitable. Said acid and anhydride forms of AVE/MA copolymers, having an average molecular weight of from about 50,000 to about 80,000 (as measured by membrane osmometry in 2-butanone 1-10 grams/1000 ml solution), are also characterized by having the previously described specific viscosity parameter of more than 1.2. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

In general, the lower alkyl vinyl ether-maleic acid copolymer (I), or its corresponding anhydride, is added to water preheated to about 70°–80° C. with vigorous stirring to form a homogeneous mixture. If the anhydride precursor is utilized, it is recommended that the aqueous mixture be further heated to about 90° C. with stirring to ensure complete hydrolysis of the anhydride to the acid form. Heating is then discontinued although mixing is continued until the batch turns clear with a simultaneous decrease in viscosity (about 65°–75° C.). An aqueous solution of the cationic zinc or strontium salt forming compound, or, for example, an aqueous dispersion of particulate zinc oxide in the form of a slurry, in an amount sufficient to provide the desired cationic content desired in the end-product, is separately prepared at ambient temperature and slowly added to the hot polymeric acid solution with continuous vigorous mixing so as to prevent localized precipitation of the cationic polymeric salt. After addition is complete, mixing is continued to ensure that all the salt forming compound is reacted with the copolymer.

The sum total of zinc or strontium cations in the resultant unmixed partial salts of AVE/MA copolymers should be sufficient to give a neutralization of from about 10 to about 60 percent and preferably from about 40 to about 50 percent of the total initial carboxyl groups in the copolymer.

The reaction batch is then transferred to shallow drying trays in a convection oven maintained at about 70° C. with hot air circulation to evaporate the water content and recover the polymeric salt product in dry form. If necessary, the reaction solution may be treated according to conventional purification methodology to remove or minimize any contaminants occasioned by anionic functions in the aforementioned cationic zinc or strontium salt forming compound.

After drying, the resultant product, which consists essentially of the particular zinc or strontium unmixed partial salt of the AVE/MA copolymer, is then ground or milled to the desired mesh size for providing the satisfactory denture-stabilizing properties and physical characteristics of the invention. Said salts are frangible so that appropriate particle size and bulk density can be obtained. For best results, particles should be capable of passage through a 140- to 200-mesh sieve (U.S.B.S. series) and preferably are less than 0.74 millimeter in their largest dimension.

The subject zinc and strontium AVE/MA copolymer salts have exceptional adhesive qualities when contacted with water or saliva such that they are extremely useful as denture adhesive materials in denture-stabilizing compositions. For such use the salt in particulate form is preferably characterized by a particle size of at least minus 140-mesh U.S.B.S. sieve; a bulk density greater than 0.5 gram per cubic centimeter and preferably higher than 0.7 gram per cubic centimeter; and a pH between 3 and 4.7, the pH being determined on a one percent by weight dispersion in water.

Each of the subject zinc and strontium AVE/MA copolymer salts may be utilized in effective adhesive amounts, preferably at least 25 percent by weight, as the sole adhesive component or as a co-adhesive in joint usage with other active adhesive components in denture-stabilizing compositions. With regard to the zinc copolymer salt, however, because of physiological limitations inherent in the constant daily usage of zinc containing ingestible products, including oral hygiene products such as denture stabilizing compositions, whereby the recommended dietary allowance (RDA) of 15 mg per day for adults (reference: Kirk-Othmar's "Encyclopedia of Chemical Technology", Publ. by John Wiley & Sons, New York, N.Y. 1984, 3rd Ed., Vol. 24, page 859) should not be exceeded, it is preferred that said zinc copolymer salt be used as a co-adhesive with other suitable denture adhesives in denture-stabilizing compositions in an amount sufficient to provide an elemental zinc content, based on the total weight of the composition, ranging from about 1.0 to about 2.5 percent and, preferably, from about 1.4 to about 1.9 percent. In general, from about 5 to about 35 percent, based on the total weight of the composition, of said zinc copolymer salt is sufficient to provide said elemental zinc content, calculated with reference to the average amount (0.8 gram) of the denture-stabilizing cream form as a standard.

Denture-stabilizing compositions generally include, as the active adhesive element, either a water-soluble or partially water-soluble hydrophilic colloid or polymer having the particular property of swelling upon exposure to moisture to form a mucilaginous mass. Such adhesive materials include both natural gums and synthetic polymeric gums and, among those commonly employed in denture-stabilizing compositions and which are also suitable herein co-adhesive action with the subject zinc and strontium AVE/MA copolymer salts, there may be mentioned, for example, karaya gum, gelatin, algin, sodium alginate, tragacanth, methylcellulose, acrylamide polymers, ethylene oxide polymers, polyvinylpyrrolidone, cationic polyarylamide polymers and, as the most preferred, sodium carboxymethylcellulose and mixed partial salts of poly(vinyl methyl-ether maleate).

Accordingly, a preferred aspect of the subject invention provides an improvment in a denture-stabilizing composition comprising an effective adhesive amount of at least two denture adhesive components, the improvement comprising having, as one of said components, from about 5 to about 35 percent, based on the total weight of the composition, of a water-insoluble water-sensitized polymeric material characterized by a particle size of at least minus 140-mesh U.S.B.S. sieve, by an apparent bulk density greater than 0.5 gram per cubic centimeter, and a pH between 3 and 4.7, the pH being determined on a one percent by weight dispersion of said material in water; said material consisting essentially of an unmixed partial zinc metal salt of a lower alkyl vinyl ether-maleic acid copolymer consisting essentially of the repeated structural unit:

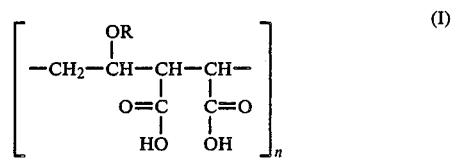

(I)

wherein R represents $C_{1-4}$ alkyl, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salt containing zinc cation as the sole cationic salt function, with from about 10 to about 60 percent of the total initial carboxyl groups reacted with said zinc cation; said partial zinc copolymer salt being present in an amount, based on the total weight of the composition, sufficient to provide from about 1.0 to about 2.4 percent of elemental zinc.

It has been surprisingly found that the subject zinc and stronium salts of AVE/MA copolymers are particularly useful as a co-adhesive in denture adhesive compositions when used in combination with the mixed partial salts of lower alkyl vinyl ether-maleic anhydride-type copolymers described in the previously identified U.S. Pat. No. 3,003,988, incorporated herein by reference. For purposes of convenience, claim 1 of said patent is quoted hereinbelow:

Beginning of Quote: claim 1 of U.S. Pat. No. 3,03,988
"A denture-stabilizing composition having as a stabilizing component a material comprising more than 25 percent by weight of said denture-stabilizing composition and being a water-insoluble water-sensitized polymeric material; said material characterized by a particle size of minus 150-mesh U.S.B.S. sieve, by an apparent bulk density greater than 0.5 gram per cubic centimeter, and by a pH between 5 and 8.5, the pH being determined on a one percent of weight aqueous dispersion of said material in water; said material consisting essentially of a partial mixed salt of a copolymer selected from the group consisting of copolymers and partial lower alkyl esters of these copolymers, said copolymers consisting essentially of the repeated structural unit,

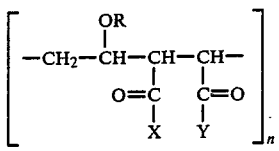  (I)

wherein X and Y separately each represent a hydroxyl radical and X and Y together represent a bivalent oxygen atom, R represents an alkyl radical of less than 5 carbon atoms, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial lower alkyl esters of said copolymers having less than one-third of the total initial carboxyl groups esterified, said partial mixed salts containing calcium cations and alkali cations, in a mole ratio between 1:1 and 5:1, the alkali cations selected from the group consisting of sodium, potassium and quaternary ammonium cations, with not more than one third of the total initial carboxyl groups unreacted."

End of Quote

Of the mixed partial copolymeric salts and esters described in Claim 1 of said U.S. Pat. No. 3,003,988, the salts are preferred, particularly the calcium-sodium (Ca/Na) salts, for combined usage with the unmixed partial zinc or strontium copolymeric salts herein described. The most preferred salts of said U.S. Pat. No. 3,003,988 are the calcium-sodium partial salts of methyl vinyl ether-maleic anhydride copolymer with about 20-36 percent of the total initial carboxyl groups of the copolymer unreacted, a calcium-to-sodium ratio of from about 2.5:1 to about 4:1 per initial carboxyl group, an apparent bulk density of about 0.5 gram per cubic centimeter as a minimum and substantially from about 0.7 to about 0.9 gram per cubic centimeter, and a pH of about 6-7.5 for the powder at a concentration of 1 percent by weight in water. Said methyl vinyl ether-maleic anhydride copolymer is also denoted as poly(vinyl methyl-ether maleate), sometimes abbreviated hereinafter as "PVM/EM".

In Example VI of the aforementioned U.S. Pat. No. 3,003,988, a calcium-sodium partial salt of methyl vinyl ether-maleic anhydride copolymer is described with about 30 percent of the total initial groups of the copolymer unreacted, a calcium-to-sodium equivalent ratio of 0.51:0.19 (i.e., about 2.6:1) per initial carboxyl group, an apparent bulk density of 0.88 gram per cubic centimeter, and a pH of 7.5 for the powder at a concentration of 1 percent by weight in water. This particular 2.6:1 Ca:Na partial salt, which is among the preferred, mixed partial salts utilized in this invention, will be referred to hereinafter by the abbreviated term, "2.6:1 Ca:Na partial salt of PVM/EM copolymer."

The preparation of another preferred Ca/Na partial salt is shown in Example VII of the '988 patent, wherein the calcium-to-sodium equivalent ratio is 0.5:0.134 (i.e. about 3.75:1), with about 35 percent of the total initial groups of the copolymer unreacted, an apparent bulk density of 0.92 gram per cubic centimeter, and a pH of 6.2 for the powder at a concentration of 1 percent by weight in water. This particular 3.75:1 Ca:Na partial salt will be referred to hereinafter by the abbreviated term, "3.75:1 Ca:Na partial salt of PVM/EM copolymer".

Among the most preferred Ca/Na partial salts of methyl vinyl ether-maleic anhydride copolymer is the calcium-sodium partial salt with about 20 percent of the total initial carboxyl groups of the copolymer unreacted, a calcium-to-sodium equivalent ratio of about 3.5:1 per initial carboxyl group, an apparent bulk density of about 0.8-0.95 gram per cubic centimeter, and a pH of about 6.3-7.4 for the powder at a concentration of 1 percent by weight in water. This particular 3.5:1 Ca:Na partial salt will be referred to hereinafter by the abbreviated term, "3.5:1 Ca:Na partial salt of PVM/EM copolymer.

The most preferred Ca/Na partial salts may be obtained by following the procedures of the aforementioned Examples VI and VIII of the '988 patent by, for example, utilizing aqueous solutions of sufficient calcium acetate and sodium hydroxide (via Example VI) or calcium acetate and sodium acetate (via Example VIII) to yield the desired Ca:Na ratio upon reaction with the appropriate methy vinyl ether-maleic anhydride copolymer.

In accordance with this invention, therefore, the adhesive characteristics of the foregoing denture-stabilizing compositions of said U.S. Pat. No. 3,003,988, and preferably those containing the Ca/Na partial mixed copolymer salts thereof, are markedly improved by the coadhesive action of the zinc (prefered) or strontium partial unmixed copolymer salts herein described.

Accordingly, another preferred aspect of this invention provides an improvement in a denture-stabilizing composition containing an effective adhesive amount of at least two denture adhesive components, one of such components being a calcium-sodium mixed partial salt of methyl vinyl ether-maleic anhydride-type copolymer, which improvement comprises having, as a second such component, from about 5 to about 35 percent, based on the total weight of the composition, of a water-insoluble water-sensitized polymeric material characterized by a particle size of at least minus 140-mesh U.S.B.S. sieve, by an apparent bulk density greater than 0.5 gram per cubic centimeter, and a pH between 3 and 4.7, the pH being determined on a one percent by weight dispersion of said material in water; said material consisting essentially of an unmixed partial zinc metal salt of a lower alkyl vinyl ether-maleic acid copolymer consisting essentially of the repeated structural unit:

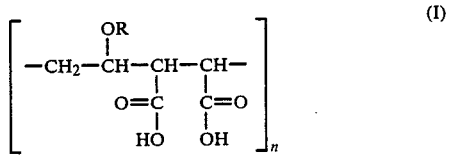 (I)

wherein R represents $C_{1-4}$ alkyl, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salt containing zinc cation as the sole cationic salt function, with from about 10 to about 60 percent of the total initial carboxyl groups reacted with said zinc cation; said partial zinc copolymer salt being present in an amount, based on the total weight of the composition, sufficient to provide from about 1.0 to about 2.4 percent of elemental zinc.

EXAMPLE 1

Into a reaction vessel equipped with a high speed stirrer and containing 73.5 parts (29.9 kg) of purified water heated to 70° C., is slowly added 3.87 parts (1.58 kg) of methyl vinyl ether-maleic anhydride copolymer having a specific viscosity of about 2.5. After addition is complete, the temperature of the aqueous copolymer dispersion is raised to 90°-95° C. with high speed mixing. At such temperature, hydration of the anhydride copolymer continues marked by a significant increase in batch viscosity. Further heating is then discontinued and the mixture is gradually cooled to about 70° C. with continued mixing. Complete hydrolysis of the anhydride copolymer to the corresponding methyl vinyl ether-maleic acid (MVE/MA) copolymer is observable when the batch turns clear with a substantial and simultaneous decrease in viscosity.

In a separate vessel 1.04 parts (422.7 grams) of zinc oxide is thoroughly dispersed in 21.6 parts (1.58 kg) of purified water. The aqueous zinc oxide dispersion is added slowly to the hot MVE/MA copolymer solution in small quantities. Vigorous stirring of the MVE/MA copolymer solution is required to prevent localized precipitation of the zinc MVE/MA copolymer salt. After addition of the zinc oxide dispersion is complete, mixing is continued for about another two hours to ensure completion of the reaction.

The resultant solution of the zinc salt of methyl vinyl ether-maleic acid (MVE/MA) copolymer is then transferred to shallow stainless steel drying trays and the trays placed in a hot air convection oven at 70° C. for a sufficient time to evaporate the water content (about 16-18 hours). The thus obtained dried zinc MVE/MA copolymer salt is then ground in a milling apparatus and screened through a 140-mesh sieve and then through a 200 mesh sieve (U.S.B.S. sieve series). The powder has an apparent bulk density of about 0.9-1.1 gram per cubic centimeter, and a pH of 4.6 for a one percent solution in water. Analysis of the salt indicates about 50 percent neutralization with zinc of the total initial carboxyl groups in the copolymeric salt molecule. This particular 50% neutralized zinc salt will be referred to hereinafter by the abbreviated term "50% Zn partial salt of MVE/MA copolymer".

The product, when used in conjunction with conventional denture adhesives and applied to wet dentures with normal usage, provides denture stabilizing characteristics superior to those obtained by the particular conventional denture adhesive itself.

In accordance with the foregoing procedure, the corresponding 50% neutralized zinc salt of ethyl vinyl ether-maleic acid (EVE/MA) copolymer is obtained by substituting an equivalent amount of ethyl vinyl ether-maleic anhydride copolymer for the methyl anhydride copolymer starting material.

EXAMPLE 2

The procedure of Example 1 is repeated except that the following amounts of reactants are employed:
a. 4.07 parts (1.66 kg) of the anhydride copolymer in 77.30 parts (31.52 kg) purified water; and
b. 0.85 parts (346.6 grams) of zinc oxide in 17.78 parts (7.25 kg) purified water.

The resultant powder has an apparent bulk density of about 0.9-1.1 gram per cubic centimeter and a pH of 4.2 for a one percent solution in water. Analysis of the salt indicates about 40 percent zinc neutralization of the total initial carboxyl groups in the copolymer salt molecule. This particular 40% neutralized zinc salt will be referred to hereinafter by the abbreviated term "40% Zn partial salt of MVE/MA copolymer".

The product, when applied to wet dentures, has stabilizing characteristics superior to those of commercial denture stabilizers.

EXAMPLE 3

By following the general procedure of Example 1, except that an appropriate amount of zinc oxide is utilized to provide the tabulated zinc substitution, the following zinc salts of MVE/MA copolymer are obtained having the indicated pH:

| % Neutralization of —COOH Groups | pH of 1% Solution |
|---|---|
| 10 | 3.01 |
| 20 | 3.45 |
| 30 | 3.85 |
| 60 | 4.67 |

Each of the indicated zinc MVE/MA copolymer salts, having an apparent bulk density for the minus 140-mesh U.S.B.S. sieve powder greater than 0.5 gram per cubic centimeter, provides markedly beneficial denture stabilizing characteristics. Each of the indicated salts may be abbreviated by the % Zn neutralization as done in Examples 1 and 2.

EXAMPLE 4

A. The MVE/MA copolymeric anhydride-to-acid hydrolysis procedure outlined in Example 1 is repeated. In a separate vessel 1.20 parts (475.2 grams) of strontium hydroxide octahydrate is dissolved in 24.9 parts (9.96 kg) of purified water. With vigorous stirring of the hot MVE/MA copolymer solution, the strontium hydroxide solution is added slowly in small quantities. After addition of the strontium hydroxide solution is complete, mixing is continued for another two hours. The resultant solution of strontium MVE/MA copolymer salt is then dried as in Example 1 and the thus obtained salt, with about 20 percent strontium neutralization, is milled to a particle size of minus 140-mesh U.S.B.S. sieve. The apparent bulk density is greater than 0.7 gram per cubic centimeter and the pH is between 3 and 4.7.

B. Additional strontium partial salts of MVE/MA copolymer with varying percentages between 10 and 60 percent of strontium cation neutralization of the initial —COOH groups in the copolymer molecule are readily obtained by utilizing the appropriate amount of strontium hydroxide in accordance with the general procedure of this example.

EXAMPLE 5

Denture-stabilizing powder compositions are prepared by blending together the following:

|  | % w/w |
|---|---|
| A. Karaya gum | 53 |
| Sodium carboxymethylcellulose | 16 |
| Sodium borate | 7 |
| 2.6:1 Ca:Na partial salt of PVM/EM copolymer | 16 |
| 50% Zn partial salt of MVE/MA copolymer | 8 |
| (% Elemental zinc = 1.2%) | 100 |
| B. Sodium alginate | 55 |
| Sodium carboxymethylcellulose | 10 |
| Polyvinylpyrrolidone (average M.W. = 90,000) | 15 |
| 30% Zn partial salt of MVE/MA copolymer | 20 |
| (% Elemental zinc = 1.8%) | 100 |

EXAMPLE 6

Cream-type denture stabilizing compositions are prepared by mixing together the following:

| | % w/w | |
|---|---|---|
| | A | B |
| Mineral oil, heavy | 24.824 | 24.824 |
| Sodium carboxymethylcellulose | 22.000 | 22.000 |
| Petrolatum | 19.016 | 19.016 |
| Silicon dioxide, coloidal | 1.100 | 1.100 |
| Colorant (oil soluble red color dispersion) | 0.060 | 0.060 |
| 3.5:1 Ca:Na partial salt of PVM/EM copolymer | 20.500 | 17.750 |
| 50% Zn partial salt of MVE/MA copolymer | 12.500 | — |
| 40% Zn partial salt of MVE/MA copolymer | — | 15.250 |
| | 100.000 | 100.000 |

(% Elemental zinc: A = 1.87; B = 2.01)

EXAMPLE 7

The following cream-type denture stabilizing composition, which is prepared by mixing together the following ingredients, is used in the comparative tests of Examples 8 and 9:

|  | % w/w |
|---|---|
| Mineral oil, heavy | 26.24 |
| Sodium carboxymethylcellulose | 21.00 |
| Petrolatum | 20.10 |
| Silicon dioxide, coloidal | 1.10 |
| Colorant (oil soluble red color dispersion) | 0.06 |
| 3.5:1 Ca:Na partial salt of PVM/EM copolymer | 31.50 |
|  | 100.00 |

The compositions of this invention may be subjected to an in-vivo objective bite force measurement (gnathodynamometry) in a double-blind, crossover, comparative study on subjects having full upper and lower poorly fitted dentures. Prior to application of the test materials, a base-line bite-force measurement is obtained for each subject. Then, a standard amount of the denture adhesive composition to be tested (0.8 gram for cream; 0.3 gram for powder) is applied to the upper denture and inserted in the mouth of the subject in its normal position. The lower denture is stabilized using a standard amount (0.8 gram) of a commercially available denture adhesive cream.

Each subject is instructed to apply incisal bite force on a tuning-fork type gnathodynamometric device designed to record incisal bite force pressure sufficient to dislodge the upper denture. The incisal bite force is expressed in pounds per square inch gauge (PSIG). Measurements are taken at intervals over a representative normal daily time usage, about 7 to 9 hours. After each measurement, the dislodged upper denture is repositioned without further application of denture adhesive material to either the lower or upper denture.

The following examples demonstrate the enhanced adhesiveness obtained by the conjunctive use of the subject salts of this invention with commonly used denture adhesive materials.

EXAMPLE 8

The cream composition of Example 7, which does not contain any unmixed partial copolymer salt of this invention, is compared with the cream composition of Example 6-A in the previously described gnathodynamometric procedure. The following results are obtained:

| Cream of Example: | No. of Subjects | Pounds Biting Force, PSIG | | | | | | Total Average Biting Force PSIG |
|---|---|---|---|---|---|---|---|---|
|  |  | 0 hr. | 1 hr. | 3 hr. | 5 hr. | 7 hr. | 9 hr. |  |
| 7 | 119 | 0.17 | 5.36 | 7.02 | 8.14 | 6.79 | 6.49 | 6.82 |
| 6-A | 119 | 0.18 | 7.63 | 8.68 | 9.45 | 7.78 | 7.77* | 8.42** |

*N = 85 sub. for 9th hour reading. p value 0.01.
**N = 85, p value 0.0001.
All other readings N = 119, p value between 0.0001 to 0.008.

EXAMPLE 9

The cream composition of Example 7, which does not contain any unmixed partial copolymer salt of this invention, is compared with the cream composition of Example 6-B in the previously described gnathodynamometric procedure. The following results are obtained:

| Cream of Example: | No. of Subjects | Pounds Biting Force, PSIG | | | | | Total Average Biting Force PSIG |
|---|---|---|---|---|---|---|---|
|  |  | 0 hr. | 1 hr. | 3 hr. | 5 hr. | 7 hr. |  |
| 7 | 34 | 0.16 | 5.46 | 7.57 | 9.06 | 6.75 | 7.42 |
| 6-B | 34 | 0.16 | 6.75* | 8.25 | 9.35 | 7.87* | 8.18** |

*Significant at p < 0.003
**Significant at p < 0.08

The improved denture-stabilizing compositions of this invention, which can be produced by standard compounding techniques, can be formulated in powder, film, liquid, aerosol and cream forms which, when in contact with saliva, develop a high degree of tack and uniform viscous mucilages of high cohesive strength and which, when spread over the denture-mucosa interface, provide superior denture stabilizing properties. In addition to the denture adhesive components and a liquid, cream or powdered excipient therefor, other additives, such as, for example, any suitable flavoring agent, colorant, odorant, natural or synthetic sweetener, deodorant, antimicrobial agent, tissue healing agent or other optional ingredient generally employed as an additive in denture adhesive compositions may be utilized in the compositions of this invention, if so desired, so long as such addition is not detrimental to the overall adhesive ability of the compositions. Preferably, up to about 1.0% w/w of such additives may be utilized.

While specific examples of materials, compositions and processes have been described and illustrated, it will be apparent to those skilled in the art that a wide variety of changes and modifications may be made within the true spirit of the broadest aspects of the invention. It should be understood that the examples and the particular proportions and methods of procedure set forth are intended to be illustrative only and that the invention is to be limited only by the appended claims.

We claim:

1. The unmixed partial zinc or strontium metal salt of a lower alkyl vinyl ether-maleic acid copolymer consisting essentially of the repeated structural unit:

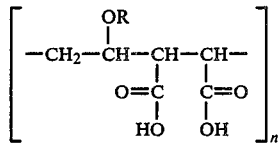

wherein R represents a $C_{1-4}$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing either zinc or strontium cations as the sole cationic salt function, with from about 10 to about 60 percent of the total initial carboxyl groups reacted.

2. The zinc salt of claim 1 with R being methyl.

3. The strontium salt of claim 1 with R being methyl.

4. The zinc salt of claim 1 with R being methyl and with from about 40 to about 50 percent of the total initial carboxyl groups reacted.

5. A denture-stabilizing composition having as a stabilizing component an effective adhesive amount of an unmixed partial zinc or strontium metal salt of a lower alkyl vinyl ether-maleic acid copolymer consisting essentially of the repeated structural unit:

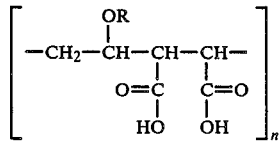

wherein R represents a $C_{1-4}$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing either zinc or strontium cations as the sole cationic salt function, with from about 10 to about 60 percent of the total initial carboxyl groups reacted.

6. The composition of claim 5 wherein said salt is the zinc salt with R being methyl.

7. The composition of claim 5 wherein said salt is the strontium salt with R being methyl.

8. In a denture-stabilizing composition comprising an effective adhesive amount of at least two denture adhesive components, the improvement which comprises having, as one of said components, from about 5 to about 35 percent, based on the total weight of the composition, of a water-insoluble water-sensitized polymeric material characterized by a particle size of at least minus 140-mesh U.S.B.S. sieve, by an apparent bulk density greater than 0.5 gram per cubic centimeter, and a pH between 3 and 4.7, the pH being determined on a one percent by weight dispersion of said material in water; said material consisting essentially of an unmixed partial zinc salt of a lower alkyl vinyl ether-maleic acid copolymer consisting essentially of the repeated structural unit:

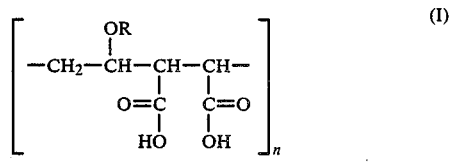

wherein R represents $C_{1-4}$ alkyl, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salt containing zinc cation as the sole cationic salt function, with from about 10 to about 60 percent of the total initial carboxyl groups reacted with said zinc cation; said partial zinc copolymer salt being present in an amount, based on the total weight of the composition, sufficient to provide from about 1.0 to about 2.4 percent of elemental zinc.

9. The composition of claim 8 wherein, with regard to said unmixed partial zinc copolymer salt, said R is methyl.

10. The composition of claim 8 wherein, with regard to said unmixed partial zinc copolymer salt, said R is methyl and from about 40 to about 50 percent of the total initial carboxyl groups are reacted.

11. The composition of claim 8 wherein said unmixed partial salt is the zinc salt, and R is methyl, and said elemental zinc content is from about 1.4 to about 1.9 percent.

12. In a denture-stabilizing composition comprising an effective adhesive amount of at least two denture adhesive components, one of such components being a calcium-sodium mixed partial salt of methyl vinyl ether-maleic anhydride-type copolymer, the improvement which comprises having, as a second such component, from about 5 to about 35 percent, based on the total weight of the composition, of a water-insoluble water-sensitized polymeric material characterized by a particle size of at least minus 140-mesh U.S.B.S. sieve, by an apparent bulk density greater than 0.5 gram per cubic centimeter, and a pH between 3 and 4.7, the pH being determined on a one percent by weight dispersion of said material in water; said material consisting essentially of an unmixed partial zinc salt of a lower alkyl vinyl ether-maleic acid copolymer consisting essentially of the repeated structural unit:

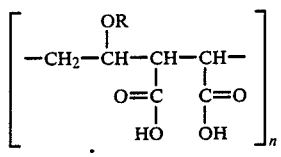 (I)

wherein R represents $C_{1-4}$ alkyl, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salt containing zinc cation as the sole cationic salt function, with from about 10 to about 60 percent of the total initial carboxyl groups reacted with said zinc cation; said partial zinc copolymer salt being present in an amount, based on the total weight of the composition, sufficient to provide from about 1.0 to about 2.4 percent of elemental zinc.

13. The composition of claim 12 wherein, with regard to said unmixed partial zinc copolymer salt, said R is methyl.

14. The composition of claim 12 wherein, with regard to said unmixed partial zinc copolymer salt, said R is methyl, and from about 40 to about 50 percent of the total initial carboxyl groups are reacted.

15. The composition of claim 12 wherein, with regard to said unmixed partial zinc copolymer salt, said R is methyl and said elemental zinc content is from about 1.4 to about 1.9 percent.

16. A denture-stabilizing composition having as a stabilizing component a material comprising at least 25 percent by weight of said denture-stabilizing composition and being a water-insoluble water-sensitized polymeric material; said material characterized by a particle size of at least 140-mesh U.S.B.S. sieve, by an apparent bulk density greater than 0.5 gram per cubic centimeter, and a pH between 3 and 4.7, the pH being determined on a one percent by weight dispersion of said material in water; said material consisting essentially of a partial unmixed zinc or strontium metal salt of a lower alkyl vinyl ether-maleic acid copolymer consisting essentially of the repeated structural unit:

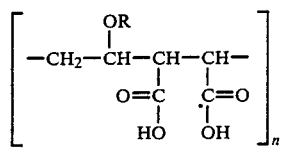 (I)

wherein R represents $C_{1-4}$ alkyl, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salt containing a member selected from the group consisting of zinc or strontium cation as the sole cationic salt function, with from about 10 to about 60 percent of the total initial carboxyl groups reacted with said cation.

17. The composition of claim 16 wherein, with regard to said unmixed partial copolymer salt, said R is methyl.

18. The composition of claim 16 wherein, with regard to said unmixed partial copolymer salt, said R is methyl and from about 40 to about 50 percent of the total initial carboxyl groups are reacted.

19. The composition of claim 16 having, as an additional adhesive component, a calcium-sodium mixed partial salt of methyl vinyl ether-maleic anhydride-type copolymer.

* * * * *